United States Patent
Bara et al.

[11] Patent Number: 5,593,680
[45] Date of Patent: Jan. 14, 1997

[54] NEW COSMETIC OR DERMOPHARMACEUTICAL COMPOSITIONS IN THE FORM OF AQUEOUS GELS MODIFIED BY THE ADDITION OF EXPANDED MICROSPHERES

[75] Inventors: Isabelle Bara, Paris; Myriam Mellul, L'Hay Les Roses, both of France

[73] Assignee: L'Oreal, Paris, France

[21] Appl. No.: 187,467

[22] Filed: Jan. 28, 1994

[30] Foreign Application Priority Data

Jan. 29, 1993 [FR] France ................. 93 00990

[51] Int. Cl.$^6$ ................... A61K 7/02
[52] U.S. Cl. ............. 424/401; 424/78.03; 514/844; 514/944
[58] Field of Search ............ 424/401, 78.03, 424/489; 428/402; 514/944, 844

[56] References Cited

U.S. PATENT DOCUMENTS

| | | | |
|---|---|---|---|
| 4,104,092 | 8/1978 | Mullay | 149/2 |
| 4,439,254 | 3/1984 | Mullay | 149/2 |
| 4,944,937 | 7/1990 | McCall | 424/65 |
| 5,053,221 | 10/1991 | Robertson et al. | 424/63 |
| 5,223,559 | 6/1993 | Arraudeau et al. | 524/47 |
| 5,246,780 | 8/1993 | Farer et al. | 428/404 |
| 5,358,719 | 10/1994 | Mellul et al. | 424/497 |
| 5,510,107 | 4/1996 | Lecomte et al. | 424/401 |

FOREIGN PATENT DOCUMENTS

| | | |
|---|---|---|
| 0486394 | 5/1992 | European Pat. Off. . |
| 1569467 | 8/1969 | Germany . |
| 2238242 | 5/1991 | United Kingdom . |

*Primary Examiner*—John C. Bleutge
*Assistant Examiner*—Robert H. Harrison
*Attorney, Agent, or Firm*—Cushman Darby & Cushman Intellectual Property Group of Pillsbury Madison & Sutro LLP

[57] ABSTRACT

A cosmetic or dermopharmaceutical composition comprises hollow microspheres dispersed in an aqueous gel which comprises a gelling agent present in an amount such that the viscosity ranges from 3 to 200 poises. The hollow microspheres are expanded thermoplastic and have a density ranging from 15 to 200 kg/m$^3$ the cosmetic or dermopharmaceutical composition contains from 0.1 to 10 percent by weight of the microspheres relative to the total weight of the composition which is free of fats.

14 Claims, No Drawings

NEW COSMETIC OR DERMOPHARMACEUTICAL COMPOSITIONS IN THE FORM OF AQUEOUS GELS MODIFIED BY THE ADDITION OF EXPANDED MICROSPHERES

The invention relates to new cosmetic or dermopharmaceutical compositions in the form of aqueous gels modified by the addition of expanded microspheres.

It is known that, in the preparation of cosmetic or dermopharmaceutical compositions, compositions in the form of emulsions, such as creams, are often used. The emulsions, which may be of the water-in-oil or oil-in-water type, consist of two immiscible phases and a surfactant whose role is to stabilize the dispersion of one of the phases, or disperse phase, in the continuous phase.

Such emulsions are generally creamy. However, depending on the amount and grade of oil employed, the user may experience a more or less unpleasant greasy effect, or even a tacky effect. In addition, the emulsifier, whose presence is necessary in order to stabilize the emulsion, can prove more or less irritant to the skin.

Moreover, some cosmetic or dermopharmaceutical compositions are presented in the form of aqueous gels. A gel is known to be an intermediate state between the solid state and the liquid state.

It is accepted that a gel consists of a three-dimensional network of molecules which retains a large amount of solvent in its meshes. Formation of such a network constitutes gelation. Depending on the nature of the solvent, hydrogels or organogels are obtained.

One of the advantages of using compositions in the form of hydrogels is that the latter give rise to a pleasant sensation of coolness on application, without a disagreeable greasy effect. However, a tacky effect and an effect of pulling of the skin are noted during an application with massage, or after application, when the water evaporates off.

It has now been discovered that, surprisingly, it is possible to obtain compositions that retain the qualities of gels without having their drawbacks, by means of the introduction of expanded hollow microspheres into a hydrophilic gel without oil. Despite the absence of oil, the modified gels thus prepared possess a lasting creaminess during application, which is especially easy and pleasant. Even after drying, the skin does not have any tacky feel and the user does not experience any sensation of pulling of the skin.

Hitherto, expanded hollow microspheres had been used in compositions in powder form, or in emulsion form, or alternatively for obtaining compositions having the appearance of a mousse; see, for example, Patents JP-60 184004, FR-2,472,382, FR-2,658,720, FR-2,669,222 or DE-2,521,003. In practice, the known cosmetic compositions employing expanded hollow microspheres always contained fats. It was not obvious that the incorporation of such microspheres into aqueous gels, without oil, would enable a creaminess to be obtained on spreading which was obtained hitherto only with compositions containing fats.

Thus, the compositions of the invention make the skin feel very comfortable and smooth on application. In addition, after application, the skin retains a matt appearance. Moreover, the compositions of the invention have a viscosity which remains substantially constant when the temperature is raised (in contrast to what is commonly observed with creams), so that their use remains pleasant even in hot countries or during hot weather.

The subject of the invention is hence a cosmetic or dermopharmaceutical composition, or a vehicle for a cosmetic or dermopharmaceutical composition, in the form of a modified gel, characterized in that the said composition or said vehicle comprises hollow microspheres dispersed in an aqueous gel, in that the said hollow microspheres are expanded microspheres made of thermoplastic material having a density of 15 to 200 kg/m$^3$, in that the said composition or said vehicle contains 0.1 to 10% by weight of the said microspheres relative to the total weight of the composition or vehicle, and in that the said composition or said vehicle is free from fats.

Expanded microspheres made of thermoplastic material are known, and may be obtained, for example, according to the processes described in Patents and Patent Applications EP-56219, EP-348372, EP-486080, EP-320473, EP-112807 and U.S. Pat. No. 3,615,972.

These microspheres may be produced from any nontoxic and non-irritant thermoplastic materials. Polymers or copolymers of acrylonitrile or of vinylidene chloride may be used, for example. It is possible to use, for example, a copolymer containing, by weight, from 0 to 60% of units derived from vinylidene chloride, from 20 to 90% of units derived from acrylonitrile and from 0 to 50% of units derived from an acrylic or styrene monomer, the sum of the percentages (by weight) being equal to 100. The acrylic monomer is, for example, a methyl or ethyl acrylate or methacrylate. The styrene monomer is, for example, alpha-methylstyrene or styrene. These microspheres can be in the dry or hydrated state.

The internal cavity of expanded hollow microspheres contains a gas, which can be a hydrocarbon such as isobutane or isopentane or alternatively air. Among hollow microspheres which can be used, special mention may be made of those marketed under the brand name EXPANCEL® (thermoplastic expandable microspheres) by the company K émanord Plast, especially those of DE (dry state) or WE (hydrated state) grade.

In the compositions or vehicles for compositions of the invention, the weight percentage of the expanded hollow microspheres is preferably between 0.5 and 5%. The texture of the gels is especially creamy with percentages of 0.5 to 2%, and generally 1 to 2% approximately. The texture is more pasty with proportions of 2 to 5%, which are more especially suited to certain skin cleansing products or to products intended for application in a thick layer (masks).

The hollow microspheres generally have average particle sizes which can vary from 5 to 250 μm, and especially from 10 to 150 μm.

To produce the gel which forms the basis of the composition or vehicle of the invention, at least one gelling agent in an aqueous liquid vehicle is used. Naturally, the gelling agent is present in a sufficient amount to endow the composition with the desired viscosity, which is obviously dependent upon the use envisaged. This viscosity can range, for example, from 3 to 200 poises (equivalent to 0.3 to 20 Pa.s).

For example, when it is desired to obtain creamy products, the viscosity is adjusted to a value between 10 and 50 poises (equivalent to between 1 and 5 Pa.s). When it is desired to produce products having a higher consistency, which can be used, in particular, as masks, the viscosity is adjusted, for example, to between 20 and 200 poises, and especially between 20 and 100 poises. For compositions used as exfoliating products for the skin (scrubs), the viscosity is, in particular, between 10 and 100 poises approximately (equivalent to between 1 and 10 Pa.s).

The gelling agents are chosen, in particular, from polymers which are water-soluble or which give colloidal solutions in water.

They are, in particular, polymers or copolymers of unsaturated organic carboxylic acids or of unsaturated esters, polysaccharide derivatives, gums, colloidal silicates, polyethylene glycols (PEG) and their derivatives, polyvinylpyrrolidones and their derivatives, polyacrylamides and their derivatives, polyacrylonitriles and hydrophilic silica gels.

The gelling agents are, for example, acrylic and/or methacrylic polymers or copolymers, vinylcarboxylic polymers, polyglyceryl acrylates or methacrylates, polyacrylamide derivatives such as SEPIGEL 305 (polyacrylamide thickener) (Seppic), PAS 5161 (water-in-oil emulsion of reticulated acrylamide/ammonium acrylate copolymer) or BOZEPOL®C (water-in-oil emulsion of reticulated acrylamide/ammonium acrylate copolymer) (Hoechst), polyacrylonitriles such as HYPAN® SS 201 (block polymer of polyacrylamide and polyacrylonitrile (Kingston/Lipo Chemical Inc.), cellulose or starch derivatives, chitin derivatives, alginates, hyaluronic acid and its salts, chondroitin sulphates, xanthan, gellan, Rhamsan, karaya or guar gum, carob flour and colloidal aluminium magnesium silicates of the montmorillonite type.

There may be mentioned especially as particular gelling agents: the vinylcarboxylic polymers sold under the name CARBOPOL® (Goodrich), acrylic acid/ethyl acrylate copolymers, acrylic acid/stearyl methacrylate copolymers, the polyglyceryl methacrylate sold under the name LUBRAJEL® (hydrate or clathrates formed by reacting sodium glycerate with a methacrylic acid polymer) (Guardian), the polyglyceryl acrylate sold under the trade name HISPAGEL (glyceryl polyacrylate) (Hispano Chimica), carboxymethylcellulose, hydroxymethylcellulose, hydroxypropylcellulose, microcrystallinecellulose, hydroxypropyl guar, the colloidal hectorites or bentonites sold under the trade name VEEGUM® (magnesium aluminum silicate), and the like.

The compositions of the invention can also contain the various ingredients used in cosmetic or dermopharmaceutical compositions, in particular pigments, dyes, preservatives, hydrating agents, perfumes, texturing agents such as pulverulent agents other than hollow microspheres, ultraviolet-absorbing agents, and the like.

The pigments can be inorganic pigments, organic pigments, or nacreous pigments. Among inorganic pigments, titanium dioxide, black, yellow, red or brown iron oxide, manganese violet, ultramarine violet, ultramarine blue, chromium oxide, and the like.

Among organic pigments, special mention may be made of the pigments D & C Red No. 3, No. 6, No. 7, No. 9, No. 13, No. 19, No. 21, No. 27, No. 30 or No. 36, or alternatively carbon black.

The nacreous pigments may be chosen from white nacreous pigments such as mica coated with titanium oxide or with bismuth oxychloride. It is also possible to use colored nacreous pigments such as titanium mica colored with iron oxides or with chromium oxide, titanium mica colored with an organic pigment of the abovementioned type or alternatively nacreous pigments based on bismuth oxychloride.

As dyes, it is possible to use water-soluble dyes such as Ponceau disodium salt, alizarin green disodium salt, quinoline yellow, amaranth trisodium salt, tartrazine disodium salt, rhodamine monosodium salt, fuchsin disodium salt, xanthophyll, and the like.

Among the water-soluble ingredients which can be used, special mention may be made of polyols such as propylene glycol, 1,3-butylene glycol, glycerol, polyglycerol, sorbitol, glucose, sucrose, magnesium glucohate, trace elements, water-soluble silicone acids, and the like.

Some compositions of the invention (in particular makeup or cleansing products) can also contain pulverulent fillers, especially clays of the montmorillonite, hectorite or bentonite type for the cleansing products, or other fillers such as silicas or silicone powders (trade name TOSPEARL) or polyamides (nylon) or powdered polymethyl methacrylate (trade name MICROPEARL®) to obtain optical effects.

There may also be mentioned various white fillers customarily used in cosmetology, such as, for example, talc, kaolin, powdered TEFLON® (polytetrafluoroethylene), powdered polyethylene, powdered crosslinked poly-beta-alanine, and the like.

To prepare the compositions of the invention, the soluble ingredients are dissolved, or the insoluble active agents are dispersed, in the aqueous liquid medium, and the gelling agent or agents is/are then added. The expanded hollow microspheres are then introduced. The fillers may be added before or after the introduction of the gelling agent. The process necessitates neither vigorous agitation nor a supply of heat if all the compounds are soluble at room temperature. There will thus be no problem in using gels that are sensitive to shearing and temperature-sensitive ingredients.

Among the compositions (or vehicles) of the invention, those having good qualities of creaminess are, in particular, those which contain 0.1 to 2%, and especially 0.5 to 1%, by weight of expanded hollow microspheres relative to the total weight of the composition, the said microspheres being 5–50 μm, and especially 10–30 μm, in size. Such compositions constitute, in particular, in the form of creamy gels, products for care of the face (including masks) or of the body, sun gels, after-shave products, makeup products of the makeup foundation, blusher or eyeshadow type, or makeup removal products.

The compositions constituting a skin cleansing product in the form of a face mask contain, for example, 2 to 5% by weight of hollow microspheres 10 to 50 μm in size.

The exfoliating compositions for the skin (scrubs) contain, for example, 0.5 to 5% by weight of expanded hollow microspheres, the said microspheres having average sizes of 80 to 250 μm, and especially 100 to 250 μm.

The dermopharmaceutical compositions according to the invention are pharmaceutical compositions applied locally to the skin or mucosae.

These compositions can contain at least one active agent intended, in particular, for the treatment or prevention of skin disorders including ache, mycoses, seborrhoeic dermatitis, eczema, rosacea, solar dermatoses and skin ageing, or alternatively scalp disorders.

Among active agents, there may be mentioned, by way of example:

agents which modulate cutaneous pigmentation and/or differentiation and/or proliferation, such as compounds whose action is mediated via nuclear receptors of the superfamily of steroids/thyroid hormones, especially retinoic acid, its isomers and its derivatives, for example retinol or its esters, as well as analogous synthetic compounds, for example 6-[3-(1-adamantyl)-4-methoxyphenyl]-2-naphthoic acid; vitamin D or its derivatives, such as 1,25-dihydroxyvitamin $D_3$ or calcipotriol; estrogens such as estradiol;

antibiotic agents such as clindamycin phosphate, erythromycin or antibiotics of the tetracycline class, for example minocycline;

antibacterials, especially benzoyl peroxide;

antimicrobials, especially metronidazole;

antifungals, especially compounds belonging to the imidazole family such as econazole or omoconazole or their salts, polyene compounds such as amphotericin B, or compounds of the allylamine family such as terbinafine;

steroidal anti-inflammatory agents such as hydrocortisone, betamethasone valerate or clobetasol propionate, or non-steroidal anti-inflammatory agents such as ibuprofen or diclofenac and their salts;

antipruritic agents such as capsaicin or lithium salts;

analgesic agents;

antiviral agents such as acyclovir;

ion channel blockers such as minoxidil and its derivatives;

keratolytic agents such as alpha-hydroxy- or beta-ketocarboxylic acids, their salts, amides or esters, and more especially alpha-hydroxy acids such as glycolic acid or citric acid;

anti-free-radical agents such as alphatocopherol or its esters, superoxide dismutases or certain metal-chelating agents.

The concentration used in the dermopharmaceutical compositions depends on the nature of the active agent; it is generally between 0.001 and 30% by weight of the composition.

The subject of the invention is also the use of hollow microspheres as are defined above, as additives intended for improving the ease and gentleness of application of an aqueous cosmetic or dermopharmaceutical gel free from fats.

The subject of the invention is also a cosmetic treatment process, characterized in that a cosmetic composition as defined above is applied to the skin.

The dermopharmaceutical compositions of the invention may be used, in particular, in a therapeutic treatment process comprising the treatment or prevention of skin disorders, including solar dermatoses and skin ageing, or alternatively scalp disorders.

The examples which follow illustrate the invention.

In these examples, the percentages are by weight.

EXAMPLE 1

Skin Gel

| | |
|---|---|
| EXPANCEL ® EL 23 (KEMANORD) | 1% |
| CARBOPOL ® 954 Goodrich (Carbomer) | 1.5% |
| Polyvinylpyrrolidone | 1% |
| Polyethylene glycol | 8.4% |
| Triethanolamine | 2.5% |
| Preservative | 0.5% |
| Water | qs 100% |

This gel is prepared in the following manner: the CARBOPOL®, polyvinylpyrrolidone and polyethylene glycol are added gradually with stirring to the water containing the preservative; the mixture is neutralized with the triethanolamine and the EXPANCEL® is then introduced at room temperature.

Result: A very smooth, creamy, non-greasy and non-tacky skin care gel is obtained.

| Characteristics of EXPANCEL ® EL 23: | |
|---|---|
| Average particle size: | 18 μm |
| Density: | 69.4 kg/m³ |
| Internal gas: | isobutane |

EXAMPLE 2

Blusher

In a similar manner, a gel of the following composition was prepared:

| | |
|---|---|
| EXPANCEL ® EL 23 (KEMANORD) | 1% |
| CARBOPOL ® 954 Goodrich (Carbomer) | 1.50% |
| Polyvinylpyrrolidone | 1% |
| Polyethylene glycol | 8.40% |
| Triethanolamine | 2.50% |
| Preservative | 0.50% |
| Water-soluble red dye (Ponceau disodium salt) | 0.18% |
| Water-soluble black dye (alizarin green disodium salt) | 0.22% |
| Water | qs 100% |

Result: A blusher is obtained in the form of a creamy, pinkish-red gel which is easy to apply and smooth. The makeup obtained is very natural and transparent.

EXAMPLE 3

Makeup Foundation

| | |
|---|---|
| EXPANCEL ® EL 23 (KEMANORD) | 1% |
| CARBOPOL ® 954 Goodrich (Carbomer) | 1.488% |
| Polyvinylpyrrolidone | 0.99% |
| Polyethylene glycol | 8.40% |
| Triethanolamine | 2.475% |
| Glycerol | 2% |
| Preservative | 0.30% |
| Water-soluble yellow dye (quinoline yellow) | 0.07% |
| Water-soluble red dye (Ponceau disodium salt) | 0.09% |
| Water-soluble black dye (alizarin green disodium salt) | 0.04% |
| Water | qs 100% |

Result: A makeup foundation is obtained in the form of a caramel-colored gel which spreads very easily, is absolutely non-greasy but nevertheless remains creamy and smooth. The makeup is very natural and has good resistance.

EXAMPLE 4

Scrub (Cleansing Product)

| | |
|---|---|
| EXPANCEL ® EL 16 (KEMANORD) | 1% |
| CARBOPOL ® 954 Goodrich (Carbomer) | 2% |
| Triethanolamine | 2.50% |
| Preservative | 0.50% |
| Glycerol | 3% |
| Water | qs 100% |

Result: An exfoliating product for the skin is obtained. It is applied to the skin by massaging, and the remainder of the formulation is then removed by rinsing with water. The skin is left feeling very smooth.

| Characteristics of EXPANCEL ® EL 16: | |
|---|---|
| Average particle size: | 90 μm |
| Density: | 28.8 kg/m³ |
| Internal gas: | isopentane |

EXAMPLE 5

Skin Cleansing Gel

| | |
|---|---|
| EXPANCEL ® EL 3 (KEMANORD) | 1.5% |
| CARBOPOL ® 954 Goodrich (Carbomer) | 0.95% |
| Triethanolamine | 1% |
| Butylene glycol | 5% |
| Carrageenan | 0.50% |
| Polyglycerolated dodecanediol* | 2.50% |
| Preservative | 3% |
| Water | qs 100% |

*Polyglycerolated dodecanediol: product obtained by grafting 3 mol of glycerol onto dodecanediol; see FR-2,091,516.

Result: A very smooth cleansing gel is obtained, containing large microbeads which are visible to the naked eye, having a massaging and cleansing action during application. The skin is rinsed with water as for a soap.

| Characteristics of EXPANCEL ® EL 3: | |
|---|---|
| Average particle size: | 87 μm |
| Density: | 21 kg/m³ |
| Internal gas: | isopentane |

EXAMPLE 6

Mask (Cleansing Product for the Face)

| | |
|---|---|
| EXPANCEL ® EL 4 (KEMANORD) | 5% |
| Polyvinylpyrrolidone | 2.50% |
| Polyglycerol 500 (SOLVAY) | 5% |
| Preservative | 3% |
| Water | qs 100% |

Result: A thick product of creamy appearance is obtained, which is spread on the skin in a thick layer and left to dry for 10 minutes. The product adsorbs the fats at the surface of the skin without a cooling sensation. It is removed very easily with water, leaving the skin very smooth.

| Characteristics of EXPANCEL EL 4: | |
|---|---|
| Average particle size: | 17 μm |
| Density: | 115 kg/m³ |
| Internal gas: | isobutane |

EXAMPLE 7

Aqueous Sun Gel

| | |
|---|---|
| Cellulose hydroxypropyl ether* (MW:300,000) | 3% |
| B,B'-camphorsulphonic acid (1,4-divinyl-benzene) in 33% aqueous solution | 6.06% |
| Triethanolamine, 99% | 1.2% |
| Expanded microspheres (EXPANCEL ® EL 23) | 0.5% |
| Sterilized demineralized water | qs 100% |

This gel is mild and gentle on application, and protects against solar radiation.
*Trade name KLUCEL G (Hercules)

EXAMPLE 8

After-Shave Gel

| | |
|---|---|
| Acrylic acid/stearyl methacrylate copolymer | 0.05% |
| Polyethylene glycol 800 | 2.50% |
| Glycerol | 1.50% |
| Ethanol | 38% |
| Allantoin | 0.05% |
| Menthol | 0.02% |
| Triethanolamine | 0.75% |
| Preservative | 0.01% |
| EXPANCEL ® EL 23 (KEMANORD) | 0.75% |
| Water | qs 100% |

This gel is cool, smooth and soothing.

EXAMPLE 9

In a similar manner, a dermopharmaceutical foaming scrub for skin affected by acne was prepared, its composition being as follows (% by weight):

| | |
|---|---|
| Benzoyl peroxide | 5.00 |
| CARBOPOL ® 940 (Goodrich) | 1.00 |
| Glycerol | 5.00 |
| EXPANCEL ® EL 3 | 2.00 |
| Butylene glycol | 5.00 |
| Polyglycerolated dodecanediol | 2.50 |
| Sodium hydroxide | qs pH 6 |
| Purified water | qs 100.00 |

Result: A cleansing gel suitable for the treatment of skin affected by acne is obtained. This gel is used in daily application with slight massaging, followed by a rinse with water.

EXAMPLE 10

In a similar manner, an anti-acne dermopharmaceutical gel of the following composition (% by weight) was prepared:

| | |
|---|---|
| 6-[3-(1-Adamantyl)-4-methoxyphenyl]-2-naphthoic acid | 0.10 |
| CARBOPOL ® 940 (Goodrich) | 1.10 |
| Propylene glycol | 4.00 |
| EXPANCEL ® EL 23 | 1.00 |
| Methyl para-hydroxybenzoate | 0.10 |
| Phenoxyethanol | 0.25 |
| Sodium hydroxide | qs pH 5 |
| Water | qs 100.00 |

Result: A non-greasy and non-tacky gel is obtained, which is active in daily application in the treatment of acne and in the treatment or prevention of the signs of skin ageing.

EXAMPLE 11

In a similar manner, an antifungal dermopharmaceutical gel of the following composition (% by weight) was prepared:

| | |
|---|---|
| Omoconazole nitrate | 1.00 |
| CARBOPOL ® 954 (Goodrich) | 1.50 |
| Propylene glycol | 8.40 |
| EXPANCEL ® EL 23 | 0.50 |
| Polyvinylpyrrolidone | 1.00 |
| Methyl para-hydroxybenzoate | 0.20 |

-continued

| | |
|---|---|
| Sodium hydroxide | qs pH 5 |
| Water | qs 100.00 |

Result: A gel is obtained which is active in daily application in the treatment of pityriasis versicolor and of seborrhoeic dermatitis.

EXAMPLE 12

In a similar manner, a dermopharmaceutical gel for the treatment of rosacea was prepared, its composition being as follows (% by weight):

| | |
|---|---|
| Metronidazole | 0.75 |
| CARBOPOL ® 940 (Goodrich) | 0.60 |
| Polyethylene glycol | 3.00 |
| EXPANCEL ® EL 23 | 1.50 |
| Methyl para-hydroxybenzoate | 0.10 |
| Sodium hydroxide | qs pH 5 |
| Water | qs 100.00 |

Result: A non-fatty, non-tacky gel giving a good light covering is obtained, which is active in daily application to the face in the treatment of rosacea.

EXAMPLE 13

In a similar manner, an anti-inflammatory dermopharmaceutical gel of the following composition (% by weight) was prepared:

| | |
|---|---|
| Clobetasol propionate | 0.05 |
| CARBOPOL ® 940 (Goodrich) | 0.60 |
| Propylene glycol | 20.00 |
| EXPANCEL ® EL 23 | 0.50 |
| Methyl para-hydroxybenzoate | 0.20 |
| Sodium hydroxide | qs pH 5 |
| Water | qs 100.00 |

Result: A gel is obtained which is active in daily application in the treatment of inflammatory disorders such as atopic eczema.

The comparative examples which follow show that the advantageous results achieved by adding expanded hollow microspheres to the aqueous gels are not obtained with other microspheres.

COMPARATIVE EXAMPLE No. 1

Gel Containing Silicone Resin Microbeads

This gel has the following composition (% by weight):

| | |
|---|---|
| Silicone spheres: TOSPEARL 108* (TOSHIBA) | 5% |
| CARBOPOL ® 954 GOODRICH (Carbomer) | 1.5% |
| Polyvinylpyrrolidone | 1% |
| Polyethylene glycol | 8.40% |
| Triethanolamine | 2.50% |
| Preservative | 0.30% |
| Water | 81.30% |

*TOSPEARL 108 (Trade name): this filler, of very fine particle size, is well known for contributing smoothness to aqueous cosmetic media.

Result: On application, a rapid decrease in the ease of spreading and a sticky and dry effect are observed. The product finally forms a fluff when massaging is continued.

Note: If a similar formula is prepared with 10% of TOSPEARL 108, an identical result is obtained.

COMPARATIVE EXAMPLE No. 2

Gel Containing Microporous Spheres of Polymethyl Methacrylate

| | |
|---|---|
| MICROPEARL ® M* spheres (MATSUMOTO) | 5% |
| CARBOPOL ® 954 (GOODRICH) | 1.5% |
| Polyvinylpyrrolidone | 1% |
| Polyethylene glycol | 8.40% |
| Triethanolamine | 2.50% |
| Preservative | 0.30% |
| Water | 81.30% |

*MICROPEARL ® M: microporous ultrafine spherical powder having open cavities, developed especially for cosmetic applications, very smooth to the touch for the skin; size = 10 μm Results:

Gel of attractive appearance,

Sticky on application,

Very dry effect,

Fluffy.

Note: An identical result is obtained with 10% of MICROPEARL® M.

COMPARATIVE EXAMPLE No. 3

Gel Containing Silica Microbeads with a Cavity

SB 700—Silica Beads

| | |
|---|---|
| SB 700* | 5% |
| CARBOPOL ® 954 GOODRICH (Carbomer) | 1.5% |
| Polyvinylpyrrolidone | 1% |
| Polyethylene glycol | 8.40% |
| Triethanolamine | 2.50% |
| Preservative | 0.30% |
| Water | 81.30% |

*SB 700: hydrophilic microporous powder of inorganic origin, 1 to 17 μm in size (MAPRECOS)

Results: During and after application, the feel of the skin is not pleasant.

These comparative examples demonstrate that it is not possible to obtain, even with other hollow microspheres, the cosmetic effects imparted to the aqueous gels by expanded hollow microspheres made of thermoplastic material, which have the feature of making the skin feel very smooth on application and comfortable.

We claim:

1. A cosmetic or dermopharmaceutical composition, or a vehicle for a cosmetic or dermopharmaceutical composition comprising hollow microspheres dispersed in an aqueous gel, said aqueous gel comprising at least one gelling agent selected from the group consisting of a water-soluble polymer, a polymer providing a colloidal solution in water, colloidal silicate and hydrophilic silica gel, said gelling agent being present in an aqueous vehicle in an amount such that the viscosity ranges from 3 to 200 poises, said hollow microspheres being expanded thermoplastic microspheres having a density ranging from 15 to 200 kg/m$^3$, said composition or said vehicle containing from 0.1 to 10 percent by weight of said microspheres relative to the total weight of said composition or said vehicle, said composition or said vehicle being free of fats.

2. The composition or vehicle of claim 1 wherein said hollow microspheres have an average particle size ranging from 5 to 250 μm.

3. The composition or vehicle of claim 1 wherein said hollow microspheres have an average particle size ranging from 10 to 150 μm.

4. The composition or vehicle of claim 1 wherein said gelling agent is selected from the group consisting of an unsaturated organic carboxylic acid polymer, an unsaturated organic carboxylic acid copolymer, an unsaturated ester polymer, an unsaturated ester copolymer, polysaccharide, a gum, a colloidal silicate, a polyethylene glycol, a polyvinylpyrrolidone, a hydrophilic silica gel, a polyacrylamide and a polyacrylonitrile.

5. The composition or vehicle of claim 4 wherein said gelling agent is selected from the group consisting of an acrylic polymer, a methacrylic polymer, an acrylic copolymer, a methacrylic copolymer, a vinylcarboxylic polymer, a polyglyceryl acrylate, a polyglyceryl methacrylate, a cellulose, a starch, a chitin, an alginate, hyaluronic acid, a salt of hyaluronic acid, a chondroitin sulphate, xanthan, gellan, Rhamsan, karaya or guar gum, carob flour, and montmorillonite colloidal aluminum magnesium silicate.

6. The composition or vehicle of claim 5 wherein said cellulose is selected from the group consisting of carboxymethylcellulose, hydroxymethylcellulose, hydroxypropylcellulose and microcrystallline cellulose.

7. The composition or vehicle of claim 1 in the form of a creamy gel, said creamy gel containing a gelling agent in an amount to produce a viscosity between 10 and 50 poises and said creamy gel containing said hollow microspheres in an amount ranging from 0.1 to 2 percent by weight relative to the total weight of said composition or vehicle, and said hollow microspheres having a size ranging from 5 to 50 μm.

8. The composition or vehicle of claim 7 in the form of a creamy gel, wherein said hollow microspheres have a size ranging from 10 to 30 μm.

9. The composition or vehicle of claim 1, wherein the water content of said composition ranges from 83.1% to 94.4% by weight.

10. A skin cleansing product in the form of a face mask composition comprising hollow microspheres dispersed in an aqueous gel, said aqueous gel comprising at least one gelling agent selected from the group consisting of a water-soluble polymer, a polymer providing a colloidal solution in water, colloidal silicate and hydrophilic silica gel, said gelling agent being present in an aqueous vehicle in an amount sufficient to provide a viscosity of 20–200 poises, said hollow microspheres being present in an amount ranging from 2 to 5 weight percent relative to the total weight of said composition, said hollow microspheres being expanded thermoplastic microspheres having a density ranging from 15 to 200 kg/m$^3$ and having a size ranging from 10 to 50 μm, said composition being free of fats.

11. The composition of claim 10 wherein said gelling agent is present in an amount such that the viscosity ranges from 20–100 poises.

12. An exfoliating product for the skin comprising hollow microspheres dispersed in an aqueous gel, said aqueous gel comprising at least one gelling agent selected from the group consisting of a water-soluble polymer, a polymer providing a colloidal solution in water, colloidal silicate and hydrophilic silica gel, said hollow microspheres being present in an amount ranging from 0.5 to 5 percent by weight, said hollow microspheres being expanded thermoplastic microspheres having a density ranging from 15 to 200 kg/m$^3$ and having an average size ranging from 80 to 250 μm, and said gelling agent being present in an amount providing a viscosity of 10–100 poises, said product being free of fats.

13. An exfoliating product for the skin comprising hollow microspheres dispersed in an aqueous gel, said aqueous gel comprising at least one gelling agent selected from the group consisting of a water-soluble polymer, a polymer providing a colloidal solution in water, colloidal silicate and hydrophilic silica gel, said hollow microspheres being present in an amount ranging from 0.5 to 5 percent by weight, said hollow microspheres being expanded thermoplastic microspheres having a density ranging from 15 to 200 kg/m$^3$ and having an average size ranging from 100 to 250 μm, and said gelling agent being present in an amount providing a viscosity of 10–100 poises, said product being free of fats.

14. A cosmetic treatment process comprising applying to the skin a composition comprising hollow microspheres dispersed in an aqueous gel, said aqueous gel comprising at least one gelling agent selected from the group consisting of a water-soluble polymer, a polymer providing a colloidal solution in water, colloidal silicate and hydrophilic silica gel, said gelling agent being present in an aqueous vehicle in an amount such that the viscosity ranges from 3 to 200 poises, said hollow microspheres being expanded thermoplastic microspheres having a density ranging from 15 to 200 kg/m$^3$, said composition containing from 0.1 to 10 percent by weight of said microspheres relative to the total weight of said composition, said composition being free of fats.

* * * * *